(12) United States Patent
Bhat et al.

(10) Patent No.: US 9,579,421 B2
(45) Date of Patent: Feb. 28, 2017

(54) BONE GRAFTS AND METHODS OF MAKING AND USING BONE GRAFTS

(71) Applicant: GLOBUS MEDICAL, INC, Audubon, PA (US)

(72) Inventors: Archana Bhat, Royersford, PA (US); Dan Laskowitz, Lancaster, PA (US); Patrick Joe, Royersford, PA (US); Mark Adams, Downingtown, PA (US); Michael Lee Boyer, II, Phoenixville, PA (US)

(73) Assignee: Globus Medical Inc., Audubon, PA (US)

( * ) Notice: Subject to any disclaimer, the term of this patent is extended or adjusted under 35 U.S.C. 154(b) by 58 days.

(21) Appl. No.: 14/175,184

(22) Filed: Feb. 7, 2014

(65) Prior Publication Data

US 2015/0224227 A1    Aug. 13, 2015

(51) Int. Cl.
*A61L 27/36*    (2006.01)
*A61L 27/38*    (2006.01)

(52) U.S. Cl.
CPC ......... *A61L 27/3821* (2013.01); *A61L 27/365* (2013.01); *A61L 27/3608* (2013.01); *A61L 27/3834* (2013.01); *A61L 27/3847* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,437,191 A | 3/1984 | van der Zel et al. |
| 5,681,872 A | 10/1997 | Erbe |
| 5,700,289 A | 12/1997 | Breitbart et al. |
| 5,776,193 A | 7/1998 | Kwan et al. |
| 5,854,207 A | 12/1998 | Lee et al. |
| 5,914,356 A | 6/1999 | Erbe |
| 5,939,039 A | 8/1999 | Sapieszko et al. |
| 6,123,731 A | 9/2000 | Boyce et al. |
| 6,264,701 B1 | 7/2001 | Brekke |
| 6,294,041 B1 | 9/2001 | Boyce et al. |
| 6,309,659 B1 | 10/2001 | Clokie |
| 6,350,283 B1 | 2/2002 | Michelson |
| 6,372,257 B1 | 4/2002 | Marchosky |
| 6,432,436 B1 | 8/2002 | Gertzman et al. |
| 6,437,018 B1 | 8/2002 | Gertzman et al. |
| 6,666,890 B2 | 12/2003 | Michelson |
| 6,696,073 B2 | 2/2004 | Boyce et al. |
| 6,706,067 B2 | 3/2004 | Shimp et al. |
| 6,723,131 B2 | 4/2004 | Muschler |
| 6,749,636 B2 | 6/2004 | Michelson |
| 6,752,831 B2 | 6/2004 | Sybert et al. |
| 6,776,800 B2 | 8/2004 | Boyer, II et al. |
| 6,808,585 B2 | 10/2004 | Boyce et al. |
| 6,843,807 B1 | 1/2005 | Boyce et al. |
| 6,919,308 B2 | 7/2005 | Oppermann et al. |
| 6,949,251 B2 | 9/2005 | Dalal et al. |
| 7,022,137 B2 | 4/2006 | Michelson |
| 7,041,641 B2 | 5/2006 | Rueger et al. |
| 7,132,110 B2 | 11/2006 | Kay et al. |
| 7,156,880 B2 | 1/2007 | Evans et al. |
| 7,166,133 B2 | 1/2007 | Evans et al. |
| 7,175,858 B2 | 2/2007 | Constantz et al. |
| 7,235,107 B2 | 6/2007 | Evans et al. |
| 7,262,003 B2 | 8/2007 | Kumar et al. |
| 7,275,933 B2 | 10/2007 | Jia et al. |
| 7,291,345 B2 | 11/2007 | Winterbottom et al. |
| 7,332,452 B2 | 2/2008 | Ogawa et al. |
| 7,390,498 B2 | 6/2008 | Dalal et al. |
| 7,393,405 B2 | 7/2008 | Bohner |
| 7,473,678 B2 | 1/2009 | Lynch |
| 7,494,950 B2 | 2/2009 | Armitage et al. |
| 7,498,041 B2 | 3/2009 | Masinaei et al. |
| 7,517,489 B2 | 4/2009 | Akash |
| 7,582,309 B2 | 9/2009 | Rosenberg et al. |
| 7,611,536 B2 | 11/2009 | Michelson |
| 7,723,395 B2 | 5/2010 | Ringeisen et al. |
| 7,744,597 B2 | 6/2010 | Gaskins et al. |
| 7,776,100 B2 | 8/2010 | Brekke et al. |
| 7,785,634 B2 | 8/2010 | Borden |
| 7,811,608 B2 | 10/2010 | Kay et al. |
| 7,824,702 B2 | 11/2010 | Wironen et al. |
| 7,833,278 B2 | 11/2010 | Evans et al. |
| 7,887,598 B2 | 2/2011 | Evans et al. |
| 7,892,291 B2 | 2/2011 | Evans et al. |
| 7,910,690 B2 | 3/2011 | Ringeisen et al. |
| 7,931,692 B2 | 4/2011 | Sybert et al. |
| 7,939,108 B2 | 5/2011 | Morris et al. |
| 7,942,961 B2 | 5/2011 | Asgarg |
| 7,947,759 B2 | 5/2011 | Lin et al. |
| 7,959,941 B2 | 6/2011 | Knaack et al. |
| 7,977,094 B2 | 7/2011 | Masinaei et al. |
| 8,002,813 B2 | 8/2011 | Scarborough et al. |
| 8,067,078 B1 | 11/2011 | Espinosa et al. |
| 8,093,313 B2 | 1/2012 | Miller |
| 8,105,383 B2 | 1/2012 | Michelson |
| 8,137,403 B2 | 3/2012 | Michelson |
| 8,147,860 B2 | 4/2012 | Rosenberg et al. |
| 8,147,862 B2 | 4/2012 | McKay |
| 8,163,032 B2 | 4/2012 | Evans et al. |
| 8,188,229 B2 | 5/2012 | Ringeisen et al. |
| 8,197,474 B2 | 6/2012 | Scarborough et al. |
| 8,202,539 B2 | 6/2012 | Behnam et al. |
| 8,221,781 B2 | 7/2012 | Rosenberg et al. |
| 8,232,327 B2 | 7/2012 | Garigapati et al. |

(Continued)

FOREIGN PATENT DOCUMENTS

| | | |
|---|---|---|
| CA | 1341610 C | 4/1989 |
| CA | 2027259 C | 12/2000 |
| WO | 2005084701 A1 | 9/2005 |
| WO | 2008019024 | 2/2008 |
| WO | 2010139792 | 12/2010 |
| WO | 2014128289 A1 | 8/2014 |

*Primary Examiner* — Robert Yamasaki

(57) ABSTRACT

Provided herein are bone grafts and methods of making and using the same, as well as products and kits that include such bone grafts. In particular, bone grafts are provided that include osteogenic stem cells in a mix of osteoinductive demineralized bone matrix and osteoconductive corticocancellous chips.

15 Claims, 1 Drawing Sheet

(56) References Cited

U.S. PATENT DOCUMENTS

| | | |
|---|---|---|
| 8,268,008 B2 | 9/2012 | Betz et al. |
| 8,287,915 B2 | 10/2012 | Clineff et al. |
| 8,303,967 B2 | 11/2012 | Clineff et al. |
| 8,303,971 B2 | 11/2012 | Cieslik et al. |
| 8,309,106 B2 | 11/2012 | Masinaei et al. |
| 8,323,700 B2 | 12/2012 | Morris et al. |
| 8,328,876 B2 | 12/2012 | Behnam et al. |
| 8,333,985 B2 | 12/2012 | Knaack et al. |
| 8,357,384 B2 | 1/2013 | Behnam et al. |
| 8,394,141 B2 | 3/2013 | Mills et al. |
| 8,399,409 B2 | 3/2013 | Lynch et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,435,343 B2 | 5/2013 | Yahav et al. |
| 8,435,566 B2 | 5/2013 | Behnam et al. |
| 8,454,988 B2 | 6/2013 | Rosenberg et al. |
| 8,460,686 B2 | 6/2013 | Clineff et al. |
| 8,475,824 B2 | 7/2013 | McKay |
| 8,506,981 B1 | 8/2013 | Borden |
| 8,506,985 B2 | 8/2013 | Garcia De Castro Andrews et al. |
| 8,524,265 B2 | 9/2013 | McKay |
| 8,529,962 B2 | 9/2013 | Morris et al. |
| 8,545,858 B2 | 10/2013 | Rosenberg et al. |
| 8,545,864 B2 | 10/2013 | Morris et al. |
| 8,551,519 B2 | 10/2013 | Bezwada |
| 8,551,525 B2 | 10/2013 | Cook et al. |
| 8,562,648 B2 | 10/2013 | Kaes et al. |
| 8,580,865 B2 | 11/2013 | Peters et al. |
| 8,597,675 B2 | 12/2013 | Murphy et al. |
| 8,613,938 B2 | 12/2013 | Akella et al. |
| 8,623,094 B2 | 1/2014 | Evans et al. |
| 8,641,774 B2 | 2/2014 | Rahaman et al. |
| 8,642,061 B2 | 2/2014 | Shimp et al. |
| 8,652,503 B2 | 2/2014 | Wironen et al. |
| 8,663,326 B2 | 3/2014 | Osman |
| 8,663,672 B2 | 3/2014 | Manrique et al. |
| 8,663,677 B2 | 3/2014 | Fu et al. |
| 8,685,429 B2 | 4/2014 | Koblish et al. |
| 8,734,525 B2 | 5/2014 | Behnam et al. |
| 8,740,987 B2 | 6/2014 | Geremakis et al. |
| 8,747,899 B2 | 6/2014 | Chaput et al. |
| 8,753,391 B2 | 6/2014 | Lu et al. |
| 8,753,689 B2 | 6/2014 | Morris et al. |
| 8,758,792 B2 | 6/2014 | Behnam et al. |
| 8,778,378 B2 | 7/2014 | Clineff et al. |
| 8,795,382 B2 | 8/2014 | Lin et al. |
| 8,802,626 B2 | 8/2014 | Rueger et al. |
| 8,834,928 B1 | 9/2014 | Truncale et al. |
| 8,864,843 B2 | 10/2014 | Lu et al. |
| 8,871,235 B2 | 10/2014 | Borden |
| 8,876,532 B2 | 11/2014 | Atkinson et al. |
| 8,877,221 B2 | 11/2014 | McKay |
| 8,883,210 B1 | 11/2014 | Truncale et al. |
| 8,926,710 B2 | 1/2015 | McKay |
| 8,992,964 B2 | 3/2015 | Shelby et al. |
| 8,992,965 B2 | 3/2015 | Behnam |
| 2001/0038848 A1 | 11/2001 | Donda et al. |
| 2002/0076429 A1 | 6/2002 | Wironen et al. |
| 2002/0098222 A1 | 7/2002 | Wironen et al. |
| 2002/0193883 A1 | 12/2002 | Wironen |
| 2002/0197242 A1 | 12/2002 | Gertzman et al. |
| 2003/0009235 A1 | 1/2003 | Manrique et al. |
| 2003/0055512 A1 | 3/2003 | Genin et al. |
| 2003/0149437 A1 | 8/2003 | Livne et al. |
| 2004/0091462 A1 | 5/2004 | Lin et al. |
| 2005/0118230 A1 | 6/2005 | Hill et al. |
| 2005/0251267 A1 | 11/2005 | Winterbottom et al. |
| 2005/0281856 A1 | 12/2005 | McGlohorn et al. |
| 2006/0018942 A1 | 1/2006 | Rowe et al. |
| 2006/0036331 A1 | 2/2006 | Lu et al. |
| 2006/0147545 A1 | 7/2006 | Scarborough et al. |
| 2007/0083270 A1 | 4/2007 | Masinaei et al. |
| 2007/0098756 A1 | 5/2007 | Behnam |
| 2007/0105222 A1 | 5/2007 | Wolfinbarger et al. |
| 2007/0110820 A1 | 5/2007 | Behnam |
| 2007/0113951 A1 | 5/2007 | Huang |
| 2008/0033572 A1 | 2/2008 | D'Antonio et al. |
| 2008/0069852 A1 | 3/2008 | Shimp et al. |
| 2008/0091270 A1 | 4/2008 | Miller et al. |
| 2008/0187571 A1 | 8/2008 | Clineff et al. |
| 2008/0262633 A1 | 10/2008 | Williams et al. |
| 2009/0012625 A1 | 1/2009 | Ying et al. |
| 2009/0074753 A1 | 3/2009 | Lynch |
| 2009/0157087 A1 | 6/2009 | Wei et al. |
| 2009/0192474 A1 | 7/2009 | Wei et al. |
| 2009/0238853 A1 | 9/2009 | Liu |
| 2009/0312842 A1 | 12/2009 | Bursac et al. |
| 2009/0317447 A1 | 12/2009 | Hsiao et al. |
| 2010/0055078 A1 | 3/2010 | Hughes-Fulford |
| 2010/0098673 A1 | 4/2010 | D'Antonio et al. |
| 2010/0119577 A1 | 5/2010 | Min |
| 2010/0145469 A1 | 6/2010 | Barralet et al. |
| 2010/0196333 A1 | 8/2010 | Gaskins et al. |
| 2010/0203155 A1 | 8/2010 | Wei et al. |
| 2010/0234966 A1 | 9/2010 | Lo |
| 2011/0045044 A1 | 2/2011 | Masinaei et al. |
| 2011/0066242 A1 | 3/2011 | Lu et al. |
| 2011/0070312 A1 | 3/2011 | Wei et al. |
| 2011/0117018 A1 | 5/2011 | Hart et al. |
| 2011/0117165 A1 | 5/2011 | Melican et al. |
| 2011/0117166 A1 | 5/2011 | Melican |
| 2011/0117171 A1 | 5/2011 | Melican et al. |
| 2011/0144764 A1 | 6/2011 | Bagga et al. |
| 2011/0224675 A1 | 9/2011 | Tofighi et al. |
| 2011/0262554 A1 | 10/2011 | Masinaei et al. |
| 2011/0280924 A1 | 11/2011 | Lin et al. |
| 2012/0053692 A1 | 3/2012 | Voor et al. |
| 2012/0064290 A1 | 3/2012 | Esat et al. |
| 2012/0093895 A1 | 4/2012 | Song et al. |
| 2012/0164187 A1 | 6/2012 | Ollila et al. |
| 2012/0237568 A1 | 9/2012 | Murphy et al. |
| 2013/0013071 A1 | 1/2013 | Betz et al. |
| 2013/0059382 A1 | 3/2013 | Tsai et al. |
| 2013/0122057 A1 | 5/2013 | Garigapati et al. |
| 2013/0144376 A1 | 6/2013 | Dave et al. |
| 2013/0145963 A1 | 6/2013 | Cai et al. |
| 2013/0150227 A1 | 6/2013 | Wang et al. |
| 2013/0189338 A1 | 7/2013 | Drapeau et al. |
| 2013/0195805 A1 | 8/2013 | Wei et al. |
| 2013/0202670 A1 | 8/2013 | Darmoc et al. |
| 2013/0236513 A1 | 9/2013 | Guelcher et al. |
| 2013/0244942 A1 | 9/2013 | Benedict et al. |
| 2013/0274890 A1 | 10/2013 | McKay |
| 2013/0282138 A1 | 10/2013 | McKay |
| 2013/0297038 A1 | 11/2013 | McKay |
| 2014/0010890 A1 | 1/2014 | Borden |
| 2014/0031950 A1 | 1/2014 | Cook et al. |
| 2014/0079753 A1 | 3/2014 | Darby et al. |
| 2014/0170202 A1 | 6/2014 | Peters et al. |
| 2014/0195005 A1 | 7/2014 | McKay |
| 2014/0205674 A1 | 7/2014 | Wei |
| 2014/0212471 A1 | 7/2014 | Drapeau et al. |
| 2014/0222159 A1 | 8/2014 | Bursac et al. |
| 2014/0271779 A1 | 9/2014 | Bagga et al. |
| 2014/0271786 A1 | 9/2014 | Bagga et al. |
| 2014/0271914 A1 | 9/2014 | Wagner |
| 2014/0294913 A1 | 10/2014 | Hasirci et al. |
| 2014/0314822 A1 | 10/2014 | Carter et al. |
| 2015/0010607 A1 | 1/2015 | Francis et al. |

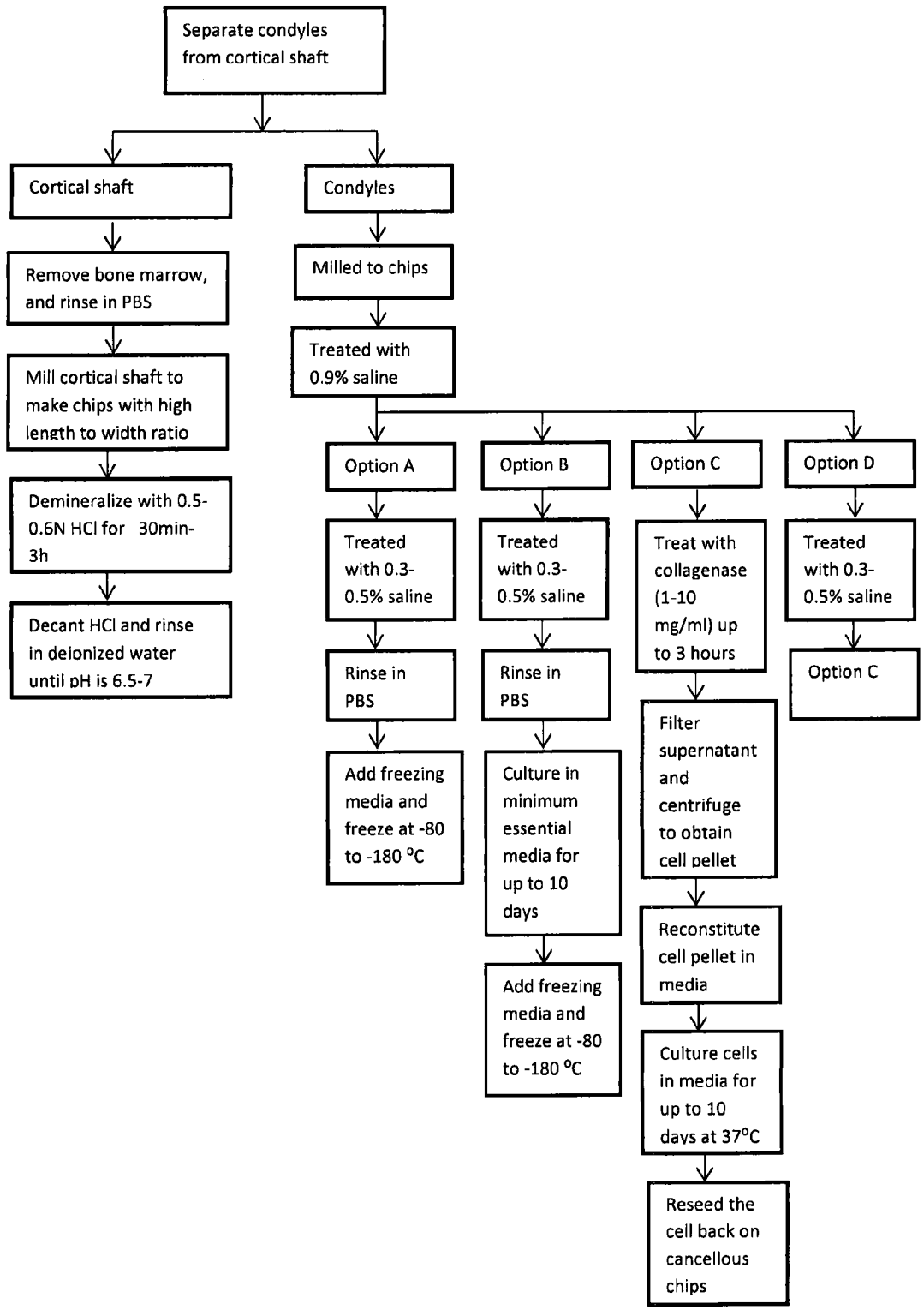

BONE GRAFTS AND METHODS OF MAKING AND USING BONE GRAFTS

FIELD OF THE INVENTION

The present invention generally relates to bone grafts, and methods of making and using the same. More specifically, the present invention relates to osteogenic bone grafts that include osteogenic stem cells in a mix of osteoinductive demineralized bone and osteoconductive cortico-cancellous chips. Further included are kits and implants having the present bone grafts; and methods of making and using the present bone grafts.

BACKGROUND

Bone generally has the ability to regenerate completely, e.g., after a fracture but requires a very small fracture space or some sort of scaffold to do so. Bone grafting is a surgical procedure that replaces missing bone to repair bone fractures that are very complex, fail to heal properly, or pose a significant health risk to the patient.

Bone grafts may be autologous (bone harvested from the patient's own body, often from the iliac crest), allograft (cadaveric bone usually obtained from a bone bank), or synthetic (often made of hydroxyapatite or other naturally occurring and biocompatible substances) with similar mechanical properties to bone. Most bone grafts are expected to be reabsorbed and replaced as the natural bone heals over a few months' time.

Bone grafts are osteogenic if they contain viable cells that are capable of bone regeneration. The current gold standard in bone graft substitutes for spine and long bone applications is autograft (i.e., using the patient's own tissue), followed by allografts. Autografts are considered osteogenic, as they contain a high number of bone forming cells. However, autographs may have limited availability and they are limited by donor site morbidity. Also, autografts may require multiple surgeries. Allografts are limited by the large variability in performance due to source and processing steps.

There is a need to produce superior bone grafts that are osteogenic and/or are able to enhance bone regeneration throughout the bone healing phase.

SUMMARY OF THE INVENTION

According to non-limiting example embodiments, the present invention provides bone grafts that include osteogenic stem cells in a mix of osteoinductive demineralized bone and osteoconductive cortico-cancellous chips, to promote bone healing.

Other example embodiments are directed to methods for preparing the bone grafts provided herein. Further example embodiments are directed to methods that include administering a bone graft substitute to a mammal by surgically inserting one or more of the present bone grafts into a mammal. The bone grafts may be administered for example by themselves e.g., in the form of a strip, putty, gel and sponge, or the bone graft may be available in conjunction with an implant, such as being incorporated therein or thereon.

Yet further example embodiments are directed to implants or other devices that include one more of the bone grafts provided herein therein or thereon. Other example embodiments are directed to kits that include one or more of the present bone grafts and/or components or ingredients that may be combined mixed or treated to prepare the present bone grafts, as well as instructions, devices, implants, tools or other components that may assist with making or using the present bone grafts.

BRIEF DESCRIPTION OF DRAWINGS

Non-limiting example embodiments are described herein, with reference to the following accompanying Figures:

FIG. 1 is a flow chart of an example method of preparing a bone graft according to non-limiting examples of the present invention.

DETAILED DESCRIPTION

The present invention is drawn to bone grafts and methods for making and using such bone grafts, as well as kits and implants or other devices including the same.

While the example embodiments are described to be used in conjunction with healing bone fractures, it should be understood that these bone grafts may be used for other purposes and therefore the present invention is not limited to such applications. In view of the teachings provided herein, one having ordinary skill in the art would recognize other applications for which the bone grafts of the present invention could be used, and would be able to use the bone grafts and methods of the present invention in other applications. Accordingly, these alternative uses are intended to be part of the present invention.

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

As used herein, the term "mammal" is intended to include any "subject" or "patient" animal, (including, but not limited to humans) to whom the present bone grafts may be administered. A subject or patient or mammal may or may not be under current medical care, and may or may not have had one or more prior treatments. As would be apparent to those skilled in the art, the formulations may be different for non-humans than for humans.

As used herein, "an effective amount" refers to an amount of the specified constituent in a composition or formulation, or an amount of the overall formulation that is effective in attaining results, the purpose for which the constituent or composition is provided. Therefore, an effective amount of a bone graft formulation would be an amount suitable for achieving the desired bone graft effect in a subject, such as a mammal (e.g., human) to which the present bone graft is administered.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

According to non-limiting example embodiments, the present invention provides bone grafts that include osteogenic stem cells in a mix of osteoinductive demineralized bone and osteoconductive cortico-cancellous chips, for example to promote bone healing in a mammal. Example embodiments provide a bone graft material that is osteogenic (in which living bone cells in the graft material contribute to bone remodeling), osteoinductive (which encourages undifferentiated cells to become active osteoblasts), and osteoconductive (which guides the reparative growth of the natural bone). Thus, example embodiments herein include bone grafts that include (1) osteogenic stem cells and (2) a mix of osteoinductive demineralized bone matrix and osteoconductive cortico-cancellous chips.

Non-limiting example embodiments also include methods of making the present bone grafts, which include (1) obtaining and/or preparing cortical chips by separating cortical bone from bone marrow, and rinsing and milling the cortical bone to chips with high length to width ratio; demineralizing the cortical chips e.g., in 0.5-0.7 N HCl for 15 min to 3 hours; removing the HCl or other treatment; and rinsing with water until the pH of the water the chips are in is between 6.5 and 7; and (2) obtaining cancellous bone chips from fresh frozen condyles which may be rinsed e.g., with saline; and further treating by one of the following methods:
 (A) treating the cancellous chips with 0.3-0.5% saline, rinsing the saline treated chips with phosphate buffered saline (PBS) (e.g., 2 or more times), mixing the chips with freezing media (e.g., minimum essential medium (MEM)) and 10% Dimethyl sulfoxide (DMSO), and freezing the chips in media and storing at temperatures between $-80°$ C. and $-180°$ C.;
 (B) treating the cancellous chips with 0.3-0.5% saline, rinsing the saline treated chips with phosphate buffered saline (PBS) (2-3 times or more); culturing the chips (e.g., in minimum essential medium), for up to 10 days; and after the culture period mixing the chips with freezing media, and freezing the chips in media and storing at temperatures between $-80°$ C. and $-180°$ C.;
 (C) treating the cancellous chips with collagenase (1 mg/ml-10 mg/ml) for 1-3 hours in an incubator set at $37°$ C. and 5% $CO_2$ with periodic agitation, forming a supernatant; filtering the supernatant through a 70 micron cell strainer; centrifuging the resulting cell suspension forming a cell pellet; reconstituting the cell pellet in cell culture media and plating in tissue culture flask; culturing the cells for up to 10 days e.g., at $37°$ C.; detaching the cells using a dissociation agent, such as trypsin and reseeding on the cancellous chips to form cell enriched cancellous chips; mixing the cell enriched cancellous chips with freezing media and storing at temperatures between $-80°$ C. and $-180°$ C.; or
 (D) treating the cancellous chips with saline as in option (A) above, and then treating and processing the chips with collagenase as in option (C) above.

Non-limiting example methods according to the present invention are depicted for example, in the flow chart of FIG. 1. As shown in FIG. 1, in example embodiments, methods of making the present bone grafts are provided, which include obtaining and/or preparing cortical chips from cortical shaft (see left side of flow chart) by removing bone marrow and rinsing in PBS, milling the cortical bone to chips with high length to width ratio; demineralizing the cortical chips e.g., in 0.5-0.6 N HCl for 30 min-3 hours; and decanting HCl; and rinsing with water until the pH of the water the chips are in is between 6.5 and 7.

The right side of the flow chart of FIG. 1 shows the four different ways that the cancellous bone chips of the present invention may be obtained. According to all of the options, cancellous bone chips are obtained from fresh frozen condyles, which are milled to chips and treated with saline. The chips are then further treated by one of the methods (Options A-D) set forth on the flow chart, which include:
 (A) treating the cancellous chips with 0.3-0.5% saline, rinsing the saline treated chips with phosphate buffered saline (PBS), and freezing the chips in media at temperatures between $-80°$ C. and $-180°$ C.;
 (B) treating the cancellous chips with 0.3-0.5% saline, rinsing the saline treated chips with phosphate buffered saline (PBS); culturing the chips (e.g., in minimum essential medium) for up to 10 days; adding freezing media, and freezing the chips in media between $-80°$ C. and $-180°$ C.;
 (C) treating the cancellous chips with collagenase (1 mg/ml-10 mg/ml) up to 3 hours; filtering supernatant and centrifuging to obtain a cell pellet; reconstituting the cell pellet in cell culture media for up to 10 days e.g., at $37°$ C.; and reseeding the cell back on cancellous chips; or
 (D) treating the cancellous chips with saline as in option (A) above, and then treating and processing the chips with collagenase as in option (C) above.

After the cortical chips and cancellous chips are obtained, the demineralized cortical chips and cell enriched cancellous chips are mixed at a ratio of about 1:1 to 2:1. This last step is not depicted in FIG. 1. This method advantageously provides a bone graft material that is osteogenic, osteoinductive and osteoconductive. According to example embodiments, the concentration of osteogenic cells in the bone graft may be more than 20,000 cells/cc of final product.

According to example embodiments, the cortical bone chips may be milled to have a relatively high length to width ratio, for example having a size of e.g., 250 microns-3 mm]. According to example embodiments, the cortical bone chips may be freeze-dried and stored at room temperature.

The cancellous chips in these embodiments may be frozen and stored at a temperature between $-80°$ C. and $-180°$ C., inclusive of the end temperatures and ranges therebetween.

Methods of Use

Also provided herein are methods that include inserting any of the present bone grafts into a mammal in need of the bone graft. By way of example, the present bone grafts may be inserted into or administered to a mammal by surgically inserting one or more of the present bone grafts into a mammal, such as a mammal in need thereof. The bone grafts may be inserted or administered for example by themselves e.g., in the form of a strip, putty, gel and/or sponge, or the bone graft may be available in conjunction with an implant, such as being incorporated therein or thereon (e.g., as a coating). The bone grafts may be inserted in an effective amount, as can be determined by a physician taking into account the need for the bone graft, the type of bone graft, and the patient.

As previously indicated, the subject/patient may be a mammal (as well as other animals), and the mammal may be (but does not have to be) human.

Embodiments of the present invention may include moldable and shapeable putty compositions that may be used for example to fill bone defects. Thus, according to example embodiments the present bone grafts may be for example in the form of a putty or other semi-solid or solid form, including, but not limited to, strip, putty, gel or sponge.

Implants

Yet further example embodiments are directed to implants or other devices or products that include one more of the bone grafts provided herein, incorporated into, or on the implant, or otherwise used with the product or implant. For example, the present bone graft substitutes may be used as a graft within or inside an implant. By way of non-limiting example, bone grafts may be used in conjunction with interbody spacers for treatment of compression fractures.

Surgical implants and compositions should be biocompatible to successfully perform their intended function. Biocompatibility may be defined as the characteristic of an implant or composition acting in such a way as to allow its therapeutic function to be manifested without secondary adverse effects such as toxicity, foreign body reaction or cellular disruption. To help avoid adverse reaction, example bone grafts may be prepared in sterile environments and formulations for implantation into a mammal.

Kits

Yet further embodiments are directed to kits that include one or more of the present bone grafts or one or more components or ingredients thereof.

Example kits may include for example, any of the present bone grafts, along with instructions and/or at least one additional component (such as devices, implants, tools) that may be used for example in the storage, preparation or use of the bone graft substitutes. By way of example, the kit components may be used to assist in adding the bone graft to a device or implant, or to assist in inserting the bone graft into a mammal. Further non-limiting examples may include one or more of the present bone grafts and instructions for the preparation of the bone graft, instructions for the use of the bone graft, a tool for insertion of the bone graft into a mammal, a tool or vehicle for hydration of a dry form of the bone graft, and/or an implant to be inserted into the mammal with the bone graft. For example, the bone graft may be provided in a syringe for reconstitution and/or administration to a mammal/patient. According to example embodiments, products may be provided in a syringe with an attachment to deliver product in a minimally invasive manner. Other possible ingredients in kits may include disposal implements or treatment literature.

Yet further non-limiting examples may include one or more ingredients of the present bone grafts, which may be combined, mixed or treated to prepare the present bone grafts. By way of example, the present kits may include cortical and/or cancellous chips in any of the stages provided herein and/or other ingredients of the present bone grafts, which may be combined, mixed or treated in order to form the present bone grafts. Further provided may be instructions for preparation of one or more of the present bone grafts and/or one or more tools, devices, implants, and/or other components to assist in making or using the present bone grafts.

The following example is provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXAMPLES

Example 1

This example demonstrates how to make example bone grafts that include osteogenic stem cells in a mix of osteoinductive demineralized bone and osteoconductive corticocancellous chips, in accordance with non-limiting example embodiments of the present invention.

The cortical and cancellous bones from long bones may be separated. The cortical bone is separated from the bone marrow, rinsed in phosphate buffered saline (PBS) solution and milled to chips (e.g., 250 microns-3 mm size with a relatively high length to width ratio). The cortical chips may then be treated with 0.5-0.7 N HCl, for 15 minutes-3 hours. At the end of the treatment, the HCl may be decanted and the chips may be rinsed in deionized (DI) water until the pH is between 6.5 and 7. The chips may then be freeze-dried and stored at room temperature.

The cancellous bone chips from fresh frozen condyles may be rinsed with 0.9% saline 2-3 times. After the rinse, the chips may be treated in one of the following ways:

(a) The cancellous chips may be treated with 0.3-0.5% saline. The saline treated chips may then be rinsed in phosphate buffered saline (2 or more times). The chips may be mixed with freezing media (minimum essential medium (MEM)) and 10% Dimethyl sulfoxide (DMSO), and frozen between −80° C. and −180° C.

(b) The cancellous chips may be treated with 0.3-0.5% saline, followed by rinsing the chips in phosphate buffered saline (2-3 times). After the rinse, the chips may be cultured in minimum essential medium, for up to 10 days. At the end of the culture period the chips may be mixed with the freezing media and frozen at a temperature between −80° C. and −180° C.

(c) The chips may be treated with collagenase (1 mg/ml-10 mg/ml) for 1-3 hours at 37° C., with periodic agitation. At the end of the time, the supernatant will be filtered through a 70 micron filter. The resulting cell suspension will then be centrifuged e.g., at 1000-1500 rpm for 5-15 minutes. The cell pellet may be reconstituted in cell culture media and plated in tissue culture flask. The cells may be cultured for up to 10 days. At the end of the time the cells may be detached using a dissociation agent and reseeded on the cancellous chips. The cell enriched cancellous chips may then be mixed with freezing media and stored at a temperature between −80° C. and −180° C.

(d) the chips may be treated with saline as in option (a), and then be treated and processed with collagenase as in option (c). The final product may be stored at between −80° C. and −180° C.

In all of the above cases, the concentration of osteogenic cells may be more than 20,000 cells/cc of final product. The final bone graft product will include demineralized cortical chips and cell-enriched cancellous chips that may be mixed at a ratio of about 1:1 to 2:1, inclusive of all points and ranges therebetween, including the end ratios.

The present invention provides a bone graft material that is osteogenic, osteoinductive and osteoconductive.

Example 2

This example exhibits another embodiment as to how to make example bone grafts that include osteogenic stem cells in a mix of osteoinductive demineralized bone and osteoconductive cortico-cancellous chips, in accordance with non-limiting example embodiments of the present invention.

The cortical and cancellous bones from long bones (such as femur, tibia, radius and ulna) may be separated. The cortical bone is separated from the bone marrow, rinsed in phosphate buffered saline (PBS) solution and processed to produce chips (e.g., 250 microns-3 mm size) with a relatively high length to width ratio. The cortical chips/fibers may then be treated with 0.5-0.7 N HCl, for 15-40 minutes. At the end of the treatment, the HCl may be decanted and the chips may be rinsed in deionized (DI) water until the pH is between 6.5 and 7. The chips may then be freeze-dried and stored at room temperature.

Condyles may be milled using a bone mill to produce cancellous chips in the range of 0.05-1.5 mm. The cancellous bone chips from fresh frozen condyles are separated, for example by being rinsed with 0.9% saline 2-3 times or more. After the rinse, the chips may be treated with 0.3-0.5% saline. The cancellous chips and the cortical fibers may be mixed in the ratio of 1:1 and mixed with freezing media (Minimum essential medium) and 10% Dimethyl sulfoxide.

This final product may be stored at temperatures between −80° C. and −180° C.

In the foregoing specification, the invention has been described with reference to specific embodiments thereof. It will, however, be evident that various modifications and changes may be made thereto without departing from the broader spirit and scope of the invention. Accordingly, it is intended that such changes and modifications fall within the scope of the present invention as defined by the claims appended hereto. The specification and drawings are, accordingly, to be regarded in an illustrative rather than restrictive sense.

We claim:

1. A method of making a bone graft, the method comprising:
   (A) obtaining and preparing demineralized cortical fibers by separating cortical bone from bone marrow, rinsing and milling the cortical bone to fibers, demineralizing the cortical fibers, rinsing the cortical fibers in water, and treating the cortical fibers to adjust the pH of the water the fibers are in to between 6.5 and 7 to form the demineralized cortical fibers;
   (B) obtaining cancellous bone chips from fresh frozen condyles by milling condyles using a bone mill to produce the cancellous bone chips having a size in the range of 0.05 to 1.5 mm and treating by a method selected from the group consisting of:
      (1) treating the cancellous chips with 0.3-0.5% saline, rinsing the saline treated chips with phosphate buffered saline, mixing the chips with freezing media and dimethyl sulfoxide (DMSO), and freezing the chips in media and storing the chips to form cell enriched cancellous chips;
      (2) treating the cancellous chips with 0.3-0.5% saline, and rinsing the saline treated chips with phosphate buffered saline; culturing the chips in medium, for up to 10 days; and after the culture period mixing the chips with freezing media and freezing the chips in media and storing the chips to form cell enriched cancellous chips;
      (3) treating the cancellous chips with collagenase in an incubator for 1-3 hours at 37° C. and 5% $O_2$ with periodic agitation, forming a supernatant; filtering the supernatant through a filter; centrifuging the filtered cell suspension for 5-15 minutes forming a cell pellet; reconstituting the cell pellet in cell culture media and plating in a tissue culture flask; culturing the cells for up to 10 days; detaching the cells using a dissociation agent and reseeding on the cancellous chips to form cell enriched cancellous chips; mixing the cell enriched cancellous chips with freezing media and storing the chips; and
      (4) treating the cancellous chips with 0.3-0.5% saline, and then treating and processing the saline treated chips as in (3) to form cell enriched cancellous chips; and
   (C) mixing the demineralized cortical fibers and cell enriched cancellous chips at a ratio of about 1:1 to 2:1; thereby providing a bone graft material that is osteogenic, osteoinductive and osteoconductive.

2. The method of claim 1, wherein the cell enriched cancellous chips are stored at a temperature between −80° C. and −180° C.

3. The method of claim 1, wherein the concentration of osteogenic cells in the bone graft is more than 20,000 cells/cc of final product.

4. The method of claim 1, wherein the cortical fibers are milled to a length to width ratio of 5:1 to 500:1.

5. The method of claim 1, wherein the cortical fibers are freeze dried and stored at room temperature.

6. The method of claim 1, wherein the cancellous bone chips are obtained from fresh frozen condyles of long bones.

7. The method of claim 1, wherein the cortical fibers have a size in the range of 250 microns to 3 mm.

8. The method of claim 1, wherein the bone graft material is in the form of a putty.

9. A method of making a bone graft comprising:
   (A) obtaining and preparing demineralized cortical fibers by separating cortical bone from bone marrow, rinsing and milling the cortical bone to fibers, demineralizing the cortical fibers, rinsing the cortical fibers in water, and treating the cortical fibers to adjust the pH of the water the fibers are in to between 6.5 and 7 to form the demineralized cortical fibers;
   (B) obtaining cancellous bone chips from fresh frozen condyles by milling condyles using a bone mill to produce the cancellous chips having a size in the range of 0.05-1.5 mm and treating by a method selected from the group consisting of:
      (1) treating the cancellous chips with 0.3-0.5% saline, rinsing the saline treated chips with phosphate buffered saline, mixing the chips with freezing media and dimethyl sulfoxide (DMSO), and freezing the chips in media and storing the chips to form cell enriched cancellous chips;
      (2) treating the cancellous chips with 0.3-0.5% saline, and rinsing the saline treated chips with phosphate buffered saline; culturing the chips in medium, for up to 10 days; and after the culture period mixing the chips with freezing media and freezing the chips in media and storing the chips to form cell enriched cancellous chips;
      (3) treating the cancellous chips with collagenase in an incubator for 1-3 hours at 37° C. and 5% $O_2$ with periodic agitation, forming a supernatant; filtering the supernatant through a filter; centrifuging the filtered cell suspension for 5-15 minutes forming a cell pellet; reconstituting the cell pellet in cell culture media and plating in a tissue culture flask; culturing the cells for up to 10 days; detaching the cells using a dissociation agent and reseeding on the cancellous chips to form cell enriched cancellous chips; mixing the cell enriched cancellous chips with freezing media and storing the chips; and (4) treating the cancellous chips with 0.3-0.5% saline, and then treating and processing the chips as in (3) to form cell enriched cancellous chips; and (C) mixing the demineralized cortical fibers and cell enriched cancellous chips at a ratio of about 1:1 to 2:1; thereby providing a bone graft material that includes osteogenic stem cells in a mix of osteoinductive demineralized cortical bone and osteoconductive cancellous chips.

10. The method of claim 9, wherein the concentration of the osteogenic stem cells in the bone graft is more than 20,000 cells/cc.

11. The method of claim 9, wherein the hone graft material is stored at a temperature between −80° C. and −180° C.

12. The method of claim 9, wherein the cortical fibers are milled to a length to width ratio of 5:1 to 500:1.

13. The method of claim 9, wherein the cortical fibers are freeze dried and stored at room temperature.

14. The method of claim 9, wherein the cortical fibers have a size in the range of 250 microns to 3 mm.

15. The method of claim 9, wherein the bone graft material is in the form of a putty.

\* \* \* \* \*